(12) United States Patent
Zand et al.

(10) Patent No.: US 8,118,206 B2
(45) Date of Patent: Feb. 21, 2012

(54) SENSING ADJUNCT FOR SURGICAL STAPLERS

(75) Inventors: Jason Matthew Zand, Washington, DC (US); Gregory Scott Fischer, Boston, MA (US)

(73) Assignee: Surgisense Corporation, Washington, DC (US)

( * ) Notice: Subject to any disclaimer, the term of this patent is extended or adjusted under 35 U.S.C. 154(b) by 303 days.

(21) Appl. No.: 12/404,276

(22) Filed: Mar. 13, 2009

(65) Prior Publication Data
US 2009/0234248 A1   Sep. 17, 2009

Related U.S. Application Data

(60) Provisional application No. 61/036,945, filed on Mar. 15, 2008.

(51) Int. Cl.
A61B 17/04 (2006.01)
A61B 17/10 (2006.01)
A61B 5/103 (2006.01)
A61B 5/117 (2006.01)

(52) U.S. Cl. ............ 227/175.1; 600/587; 600/593; 227/176.1

(58) Field of Classification Search .......... 600/300, 600/587, 593; 227/175.1–182.1
See application file for complete search history.

(56) References Cited

U.S. PATENT DOCUMENTS

| | | | |
|---|---|---|---|
| 4,945,896 A | 8/1990 | Gade | |
| 5,417,207 A | 5/1995 | Young et al. | |
| 5,503,320 A | 4/1996 | Webster et al. | |
| 5,630,539 A | 5/1997 | Plyley | |
| 5,769,791 A | 6/1998 | Benaraon et al. | |
| 5,772,597 A * | 6/1998 | Goldberger et al. | 600/473 |
| 5,785,658 A | 7/1998 | Benaraon et al. | |
| 5,807,261 A | 9/1998 | Benaraon et al. | |
| 5,833,603 A * | 11/1998 | Kovacs et al. | 600/317 |
| 5,879,294 A | 3/1999 | Anderson et al. | |
| 5,893,506 A | 4/1999 | Powell | |
| 5,987,346 A * | 11/1999 | Benaron et al. | 600/407 |
| 6,716,233 B1 | 4/2004 | Whitman | |
| 6,766,188 B2 | 7/2004 | Soller | |
| 6,959,851 B2 | 11/2005 | Heinrich | |
| 6,975,899 B2 | 12/2005 | Faupel et al. | |
| 6,981,941 B2 | 1/2006 | Whitman et al. | |
| 7,050,848 B2 | 5/2006 | Hoey et al. | |
| 7,147,138 B2 | 12/2006 | Shelton | |
| 7,237,708 B1 | 7/2007 | Guy et al. | |
| 7,407,078 B2 | 8/2008 | Shelton et al. | |
| 7,717,312 B2 * | 5/2010 | Beetel | 227/175.1 |
| 2005/0131390 A1 | 6/2005 | Heinrich et al. | |
| 2006/0235314 A1 | 10/2006 | Migliuolo et al. | |
| 2006/0273135 A1 | 12/2006 | Beetel | |
| 2007/0175949 A1 | 8/2007 | Shelton et al. | |
| 2007/0203406 A1 | 8/2007 | Anderson et al. | |
| 2008/0283570 A1 | 11/2008 | Boyden et al. | |
| 2009/0054908 A1 | 2/2009 | Zand et al. | |

FOREIGN PATENT DOCUMENTS
WO   WO 2007/008057   1/2007
* cited by examiner

*Primary Examiner* — Max Hindenburg
*Assistant Examiner* — Adam Eiseman

(57) ABSTRACT

A device and method in accordance with the invention for generating a signal indicative of a property of a subject tissue in contact with the working surface of a surgical instrument. The invention describes a sensing adjunct to surgical staplers. The adjunct can take the form of an optionally coupled accessory to a surgical stapler, or a stand-alone substitutive component acting to serve as a replacement for a component of the surgical stapler such as an anvil, housing or cartridge. Embodiments include a sensing anvil serving to act in place of a non-sensing surgical stapler anvil to monitor tissue properties of an anastomosis for the purpose of avoiding anastomotic failure.

42 Claims, 15 Drawing Sheets

SENSING ADJUNCT FOR SURGICAL STAPLERS

FIELD OF THE INVENTION

The present invention relates to surgical staplers, specifically to surgical staplers with sensors used to detect properties of biological tissue, and a system for exploiting the information gathered by the sensors.

BACKGROUND ART

A living organism is made up of cells. Cells are the smallest structures capable of maintaining life and reproducing. Cells have differing structures to perform different tasks. A tissue is an organization of a great many similar cells with varying amounts and kinds of nonliving, intercellular substances between them. An organ is an organization of several different kinds of tissues so arranged that together they can perform a special function.

Surgery is defined as a branch of medicine concerned with diseases requiring operative procedures.

Although many surgical procedures are successful, there is always a chance of failure. Depending on the type of procedure these failures can result in pain, need for re-operation, extreme sickness, or death. At present there is no reliable method of predicting when a failure will occur. Most often the failure occurs after the surgical procedure has been completed. Failures of surgical procedures can take many forms. The most difficult failures to predict and avoid are those that involve biological tissue. This difficulty arises for three distinct reasons. Firstly, the properties that favor the continued function of biological tissue are very complex. Secondly, these properties are necessarily disrupted by surgical manipulation. Finally, the properties of biological tissues vary between patients.

During a surgical operation, a variety of surgical instruments are used to manipulate biological tissues. However, traditional surgical instruments do not have the ability to obtain information from biological tissues. Obtaining information from the biological tissues that surgical instruments manipulate can provide a valuable dataset that at present is not collected. For example, this dataset can quantitatively distinguish properties of tissues that will result in success or failure when adapted to specific patient characteristics.

Surgical instruments that incorporate sensors onto the instruments' working surfaces are described, e.g., in U.S. patent application Ser. No. 10/510,940 and in U.S. Pat. No. 5,769,791. The instruments described in the prior art have the ability to sense tissue properties; however, their utility is limited by an inability to account for the multitude of differences that exist between patients. This limitation of the prior art is clearly illustrated by the fact that the instruments generate feedback after sensor signals are compared to a fixed dataset within the device. Thus, the prior art instruments have no means of adapting to patient-specific characteristics that are of utmost importance in avoiding surgical procedure failure. PCT Patent Application No. PCT/US2006/013985 describes a novel system and methodology for using the information gathered by surgical instruments having sensors in an adaptive, patient-specific manner.

Each surgical procedure has the potential for failure. A common procedure in gastrointestinal surgery is a bowel resection—removing the affected portion of the bowel and then mechanically joining the ends of the remaining segments to re-establish bowel continuity. The mechanical connection of the free ends of bowel forms what is termed a surgical anastomosis. A surgical anastomosis is formed by either traditional techniques using suture material, or by contemporary techniques utilizing surgical staplers. A surgical stapler mechanically joins the bowel by firing a pattern of staples from a cartridge or housing through the two free ends of bowel against an anvil that ultimately forms a securing crimp on the opposing side. There are many embodiments of surgical staplers. Some staplers form linear staple patterns, while others form circular patterns. Some staplers incorporate functionality for cutting tissue. Many staplers have the ability to vary the gap between the base of the staple and the formed crimp.

Anastomotic failure is one of the most feared complications of gastrointestinal surgery due to the resultant morbidity and mortality. Failure of an anastomosis, or intestinal junction, can cause a spectrum of morbidities to the patient including local abscess formation—requiring procedural drainage, tumor recurrence, debilitating pain, dysfunctional defecation, and overwhelming bacterial sepsis resulting in death. Despite improvements in surgical technique, there remains limited ability to assess the anastomotic segment and predict outcome, and as a result anastomotic failure occurs at unacceptably high levels given the severe consequences. For example, in the performance of a low anterior resection (LAR) for excision of rectal cancer, anastomotic failure has been reported to occur in up to 30% of cases. One large multicenter, observational study of 2729 patients reported a leak rate of 14.3%. These anastomotic failures cause a significant and avoidable economic burden on the healthcare system, as well as an incalculable amount of pain, suffering, and hardship for the patients in which the failure occurs. As a precaution many surgeons will avoid creating an anastomosis at the time of surgery and tunnel the free ends of the bowel through the abdominal wall to form a diverting stoma. The rationale of this maneuver is to prevent the leakage of fecal matter into the abdominal cavity from a potential anastomotic failure. Many times the surgeons will perform another procedure to reverse the stoma months after the initial procedure. In the same multicenter study 881 patients were given a temporary diverting stoma to mitigate the risk of an anastomotic leak, however, within this group only 128 patients developed a leak. Thus up to 85% of those patients underwent an additional surgical procedure to reverse the stoma that provided questionable benefit. The arbitrary creation of a temporary diverting stoma, and the eventual reversing procedure presents a significant and avoidable economic burden on the healthcare system, as well as exposes numerous patients to arguably unnecessary surgical risk. Presently, there is no reliable method or device available for predicting anastomotic failure, nor objective criteria by which to decide when a diverting stoma is indicated. Nor is there a device that can help to determine the optimal placement of an anastomosis.

There exists a need for a device, system and methodology for reducing anastomotic failures through the analysis of target tissues before, during, and after the creation of an anastomosis. There also exists a need to objectively determine, at the time of surgery, those patients that would benefit from a diverting stoma procedure. There also exists a need to deliver adjunct therapies to the anastomotic site to optimize outcome.

To accomplish its goal, the present invention couples to the desired stapling platform, which includes traditional off-the-shelf disposable surgical staplers, and uses an array of multimodality sensors to access the viability of the tissues at hand. If tissues are determined to be not suitable for an anastomosis, the present invention alerts the operative team to take corrective action, thus reducing the risk anastomotic failure.

If after performing the anastomosis, the tissues are determined to be at high risk for failure, the present invention alerts the operative team to take corrective action.

One representative application of the present invention is in the treatment of colorectal cancer. Colorectal cancer (CRC) is the third most common cause of cancer for men and women in developed countries. Estimates predict that worldwide just under 1.2 million new cases of colorectal cancer were diagnosed in 2007. Rectal cancer accounts for approximately 27% of all colorectal cancers and presents the formidable challenge of ensuring a curative resection while maintaining acceptable function. The mainstay of treatment for rectal cancer is surgical resection—removing the affected portion of the bowel and performing an anastomosis on the ends of the remaining segments to re-establish bowel continuity. The end-to-end anastomosis (EEA) is most commonly performed using circular EEA staplers. As with any surgical procedure, resection of a rectal cancer can have complications. Amongst all of the possible complications the three most devastating to the patient in terms of morbidity and mortality are tumor recurrence, anastomotic leak and anastomotic stricture. Tumor recurrence can be reduced by: following oncologic principles of dissection, providing appropriate adjunctive chemotherapeutic, photodynamic, and radiation therapies, and preventing extra-luminal extravasation of residual intra-luminal neoplastic cells through anastomotic breakdown. Anastomotic failure has been anecdotally attributed to inadequate tissue perfusion and excessive tension at the anastomosis.

When determining the location of a rectal cancer the surgeon notes the distance of the tumor from the anal verge. The anal canal extends from 0-4 cm past the anal verge, and the rectum 4-19 cm. Surgically the rectum extends from the anal sphincters to the sacral promontory. The location of the cancer dictates the type of surgical procedure performed.

The primary goal of a curative resection is to remove all potential tissues harboring cancerous cells. To accomplish this goal, the surgical team aims to resect the tumor with a cancer free margin as well as the tumor's blood supply and draining lymphatic tissue. Tumors located in the upper rectum, greater than 12 cm from the anal verge, are regularly amenable to an anterior resection (AR). Those in the mid rectum, between 6-12 cm, are subject to a LAR with or without a total mesorectal excision (TME), and tumors in the lower rectum, 4-6 cm, are usually treated with an ultra-low anterior resection (ULAR), incorporating a TME, and either a colorectal or coloanal anastomosis. A total mesorectal excision is a technique that attempts to resect the rectum and all investing soft tissues en-bloc. This technique has been touted in the literature as having superior results in terms of minimizing local tumor recurrence, however it is speculated that the procedure has an inverse effect on leak rates due to the excision of the supplying vasculature to the anastomotic site. Every attempt is made to retain fecal continence, however those tumors involving the anal sphincters 0-4 cm are resected through a sphincter sacrificing abdominoperineal resection (APR).

As a secondary goal the surgical team strives to restore continuity of the bowel and ensuing fecal stream. To accomplish this goal an anastomosis is formed. Simply, an anastomosis is the surgical connection of two free ends of a tubular structure. When the continuity of the bowel cannot be restored, the fecal stream is diverted through a stoma, or opening, in the anterior abdominal wall through which the patient eliminates into an ostomy bag. There are two main reasons for stoma formation: resection of the anal sphincter complex, and diversion of the fecal stream. In a sphincter sacrificing procedure such as an APR, the patient is dependent on a permanent ostomy. With a sphincter sparing procedure such as a LAR, the fecal stream may diverted through a temporary ostomy in order to mitigate the risk of overwhelming sepsis resulting from fecal contents entering the abdominal cavity should there be a leak at the anastomosis. Most of the time a temporary stoma can be reversed within a few months after the initial operation through a separate procedure.

Anastomotic failure can cause a spectrum of morbidities to the patient including local abscess formation—requiring procedural drainage, tumor recurrence, debilitating pain, dysfunctional defecation, and overwhelming bacterial sepsis resulting in death. The scientific literature suggests that the cause of anastomotic failure is that inadequate tissue perfusion as a result of redefined vasculature, tissue interaction forces, edema, and tension result in a decrease of oxygen delivered to the anastomotic site. Without adequate oxygen delivery efficient aerobic cell respiration cannot occur within the native cells leading to tissue degradation, collagen matrix cannot mature into strong collagen fibrils, and white blood cells cannot effectively fight bacterial invasion.

SUMMARY OF THE INVENTION

The present invention aims to reduce anastomotic failures through the analysis of target tissues before, during, and after the creation of an anastomosis. In one embodiment, the invention is an accessory for a circular stapler that allows measurement of tissue oxygenation, tissue perfusion, and tissue interaction force at twelve circumferential points around both sides of the staple joint. In one embodiment, the device incorporates three sensing modalities at each point: 1) tissue oxygenation using oximetry techniques, 2) tissue perfusion by measuring fluorescent response as fluorescein dye is injected, and 3) tissue interaction forces by utilizing MEMS pressure sensors. In addition, the staple gap height is concurrently monitored by an encoder mounted to the gap adjustment knob of the stapler. Monitoring the pressure and gap height during the creation of anastomosis provides consistency among procedures. An independent reference module with the same or similar array of sensing elements can be used concurrently to establish a baseline measurement at a tissue location independent from the surgical site.

If tissues are determined to be unsuitable for an anastomosis, the present invention alerts the operative team to take corrective action to limit the chance of anastomotic failure. Corrective actions may include any combination of the following: optimizing the location of the planned anastomosis, creating a temporary or permanent stoma, changing the operative procedure, or delivering adjunct therapies to enhance outcome.

Accordingly, several objects and advantages of the present invention are:

To provide an adjunct to a surgical stapler, where the adjunct is configured with at least one sensor that can operate independently of said stapler. The adjunct can take the form of an optionally coupled accessory to a surgical stapler, or a stand-alone substitutive component acting to serve as a replacement for a component of the surgical stapler such as an anvil.

To provide the described functionality without disrupting the surgical workflow.

To provide a sensing adjunct to a surgical stapler that is communicatively coupled to a controller or base station by wireless methods.

To reduce patient morbidity, and mortality secondary to complications, or additional procedures related to intestinal, or other tissue anastomosis.

To reduce surgical anastomotic failures, and improve outcome though the evaluation and analysis of tissues at the anastomotic site prior to, during, and after the creation of the anastomosis.

To provide the operative team an assessment of the viability of a surgical anastomosis.

To provide signal to the operative team when the creation of a diverting stoma, or change in surgical procedure is indicated.

To extend the capabilities of standard non-sensing surgical staplers to enable the sensing and analysis of subject tissues.

To enable the consistency of surgical anastomoses.

To deliver adjunct therapies to the anastomotic site.

To quantitatively monitor the staple gap or height.

To automatically adjust, or provide a signal to the operative team to adjust the staple gap or height responsive to a monitored parameter.

To assist in the firing of a surgical stapler.

To extend the capabilities of standard non-sensing surgical staplers to enable the monitoring, and/or adjustment of a staple gap or height.

To extend the capabilities of standard non-sensing surgical staplers to enable the delivery of adjunct therapies to subject tissues.

To extend the capabilities of standard non-sensing surgical staplers to enable the deployment of a tissue monitor to the anastomotic site such as described in PCT Patent Application No. PCT/US2007/071718.

To incorporate a reference module for the baseline comparison of subject tissues.

To enable tissue interrogation to generate a signal indicative of a tissue property, independently, or in conjunction with other components of the present invention.

To provide for the described functionalities in a durable, limited lifetime, or disposable manner.

To interact with a system which generates real time, patient specific procedural guidance for predicting success of a surgical anastomosis, and avoiding or detecting failure of the surgical anastomosis. Another advantage of the present invention is a system which records data across the entire patient encounter including pre-operative, intra-operative and post-operative periods, as well as immediate, acute, short term, and long term outcomes both locally in hospital-based units as well as remotely in a data repository as described in PCT Patent Application No. PCT/US2006/013985.

Additional advantages of the present invention will become readily apparent to those skilled in this art from the following detailed description, wherein only selected embodiments of the present invention are shown and described. As will be realized, the present invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent like elements throughout, and wherein.

DESCRIPTION OF THE INVENTION

Figure 1:
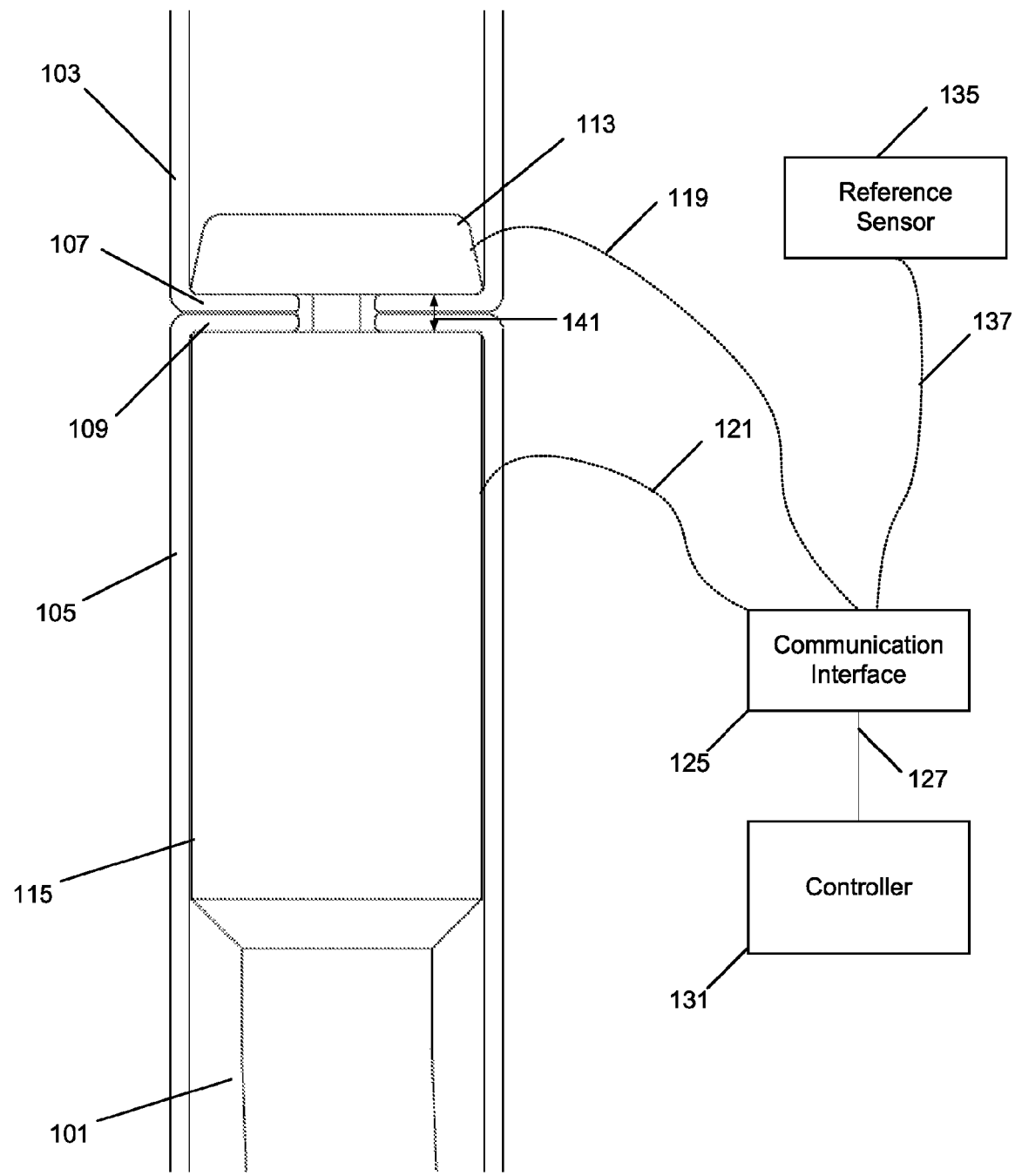
FIG. 1 shows the system overview

The present invention relates to an adjunct or accessory to a surgical stapler, where the adjunct is configured with at least one sensor that can operate independently of said stapler. The adjunct can take the form of an optionally coupled accessory to a surgical stapler, or a stand-alone substitutive component acting to serve as a replacement for a component of the surgical stapler such as an anvil. The sensors may sense mechanical or biological properties. The sensing modalities may include mechanical, optical, chemical, electrical, or other means for generating a signal indicative of a property of a subject tissue. The sensors are incorporated into or coupled to the working surface (i.e. tissue contacting surface) of an adjunct to a surgical stapler. The sensors may be incorporated into a separate accessory for the stapler affixed to either or both the anvil and housing sides of the stapler. The sensors act independently, are communicatively coupled to each other and/or a base station wirelessly. The sensors are powered by an onboard battery, capacitor, or other power storage element. Alternatively, the sensors are powered by an external source, including, but not limited to, inductive coupling, radio frequency (RF) energy, or mechanical motion.

In one embodiment of the present invention, banks of sensors are placed around the periphery of the staple line on a circular stapler. The sensors are located on one or both sides of the stapler (anvil and housing). The banks of sensors are incorporated into an accessory (i.e. a replacement part such as the anvil, or a cap/shell that optionally couples to an existing component of the stapler). The bank of sensors contains mechanical and optical sensing modalities. Mechanical sensing includes, but is not limited to, pressure sensors that monitor tissue interaction forces including compression pressure and tissue tension. Optical sensors include but are not limited to light emitters including light emitting diodes (LEDs) and laser diodes, and light receivers including photodiodes, CCD arrays, CMOS sensors, and spectrometers. The optical sensors are configured to measure at least one of tissue oxygenation, oxygen delivery, oxygen utilization, tissue characterization, and tissue general health using oximetry, or spectroscopic techniques, and at least one of tissue perfusion, tissue flow dynamics, tissue oxygen content, tissue chemical composition, tissue immunologic activity, tissue pathogen concentration, or tissue water content using fluorescence based techniques. The fluorescence based techniques include but are not limited to the following: monitoring and analyzing the intensity and time course of a fluorescent response responsive to the injection or activation of a fluorescent medium, determining oxygen quantities by measuring oxygen quenching of fluorescent radiation using a sensitive material such as Ruthenium by both intensity and time resolved methods, and determining the target tissue property by quantitative fluorescent methods including the use of quantum dots, or other fluorescent based biomarkers.

An additional element of the present invention is the incorporation of an independent reference sensor. The reference sensor contains one or more sensor banks of the same or similar type to those sensors on the working surface of the stapler. One or more reference sensors may be placed on one or more portions of the tissue to serve as a baseline measurement. In one instance, the reference sensor is placed on a healthy portion of bowel and remains in place while an anastomosis is performed on a different site. The reference may also be used as an independent sensor for preoperative or postoperative monitoring, or selection of a surgical site.

A further element of the present invention is the incorporation of a sensor that reports the staple gap or relative change thereof. In one embodiment, a sensing module is placed over the gap adjustment knob on a standard surgical stapler. The sensor incorporates an optical encoder module that interacts with a reflective encoder surface mounted to the base of the surgical stapler.

A further element of the present invention is the incorporation of a motor actuated staple gap adjustment module that will vary the staple gap responsive to at least one of user, or sensor input. The sensor input includes, but is not limited, to tissue oxygenation, compression pressure, or staple gap height. In one embodiment the motor actuated gap adjustment module is placed over the gap adjustment knob/end of a standard surgical stapler.

A further element of the present invention is the incorporation of a motor actuated stapler firing module which will fire the stapler responsive to at least one of user input, or sensor based input.

In another embodiment of the present invention, implantable sensors are placed at the surgical site to perform postoperative monitoring. The sensors may be tethered by electrical or fiber optic means, or may be wireless. Wireless sensors may be powered by an onboard source or external source.

In a further embodiment, the anvil and/or housing can act as a delivery mechanism for doses of adjunct therapies not limited to photodynamic, pharmaceutical, bio-adhesive, brachy-, and nano-therapies. The light sources used for optical sensing may also serve as an agent for activating light-sensitive treatment such as in photodynamic therapy (PDT). Alternatively the adjunct therapies can be delivered from the device to the target site through microtubules, needles, microfluidic methods, diffusion, and conduction.

In a further embodiment the reference module can act as a stand-alone tissue interrogator to determine tissue viability, or suitability for a particular procedure. The tissue interrogator can take the form of an instrument used in open or minimally invasive surgery. One representative application of the tissue interrogator embodiment is in the performance of a bowel resection secondary to a bowel obstruction. Often a bowel obstruction is caused by an adhesion which causes the bowel to twist upon itself or a hernia which incarcerates or strangulates the bowel. The blood supply to the bowel can be compromised leading to ischemia, or infarction. Intraoperatively, the surgeon qualitatively determines if the bowel is viable after it has been untwisted or freed. If the bowel does not appear viable the bowel is resected. Often qualitative methods are not accurate in determining bowel viability. An advantage of the present invention is the ability to quantitatively assess bowel viability and ensure the anastomotic joint is performed on tissue that has a minimum chance of failing due to inadequate perfusion.

The present invention will now be described in detail with reference to FIGS. 1-14.

FIG. 1 shows a representative surgical stapler augmented with sensing capabilities according to an embodiment of the present invention. This embodiment specifically depicts the augmented surgical stapler 101 for measuring properties of bowel tissue 103 and 105. Tissues 103 and 105 may represent other tissues being joined at an anastomotic site. Measurements are made at the site of the surgical anastomosis on tissue 107 and 109. The anvil sensing adjunct 113 takes measurements from the distal side of tissue 107. The housing sensing adjunct 115 takes measurements of proximal tissue 109. The sensing adjuncts 113 and 115 are coupled via wireless connections 119 and 121 respectively to a communication interface 125; alternatively the sensing adjuncts can function independently. A further reference sensor device 135 is placed outside the surgical area to capture baseline measurements. Reference sensor device 135 communicates via wireless link 137 to communication interface 125. A further gap sensing adjunct monitors the spacing between the anvil 113 and housing 115 tissue contacting surfaces to determine the staple gap height 141 and the compression of tissues 107 and 109. The gap sensing adjunct communicates wirelessly with communication interface 125. Alternatively, the sensing devices may communicate with each other as a sensor network. Further one sensing device may act as a hub that relays information to the communication interface 125. Communication interface 125 is communicatively coupled 127 to the controller 131. Controller 131 may act as a stand-alone device, or it may be connected to a database to evaluate current sensor readings responsive to past experiences. Data and outcomes may also be recorded internally or to an external database.

Depending on the sensing modality, the sensor data is translated into information that relates to tissue properties. In one exemplary optical sensing embodiment, oximetry-type techniques are used to convert the relative absorption of different wavelengths of light into an oxygen saturation percentage of hemoglobin in the blood. In another optical sensing modality, fluorescence response due to a fluorescent medium that has been introduced into the body is measured, and characteristics of the response including the intensity, rise time, and steady state value are indicative of the blood flow in the tissue in question. Further, compression pressure, and tension on tissues 107 and 109 can be measured at discrete or distributed sites on sensing adjuncts 113 and 115.

Figure 2:
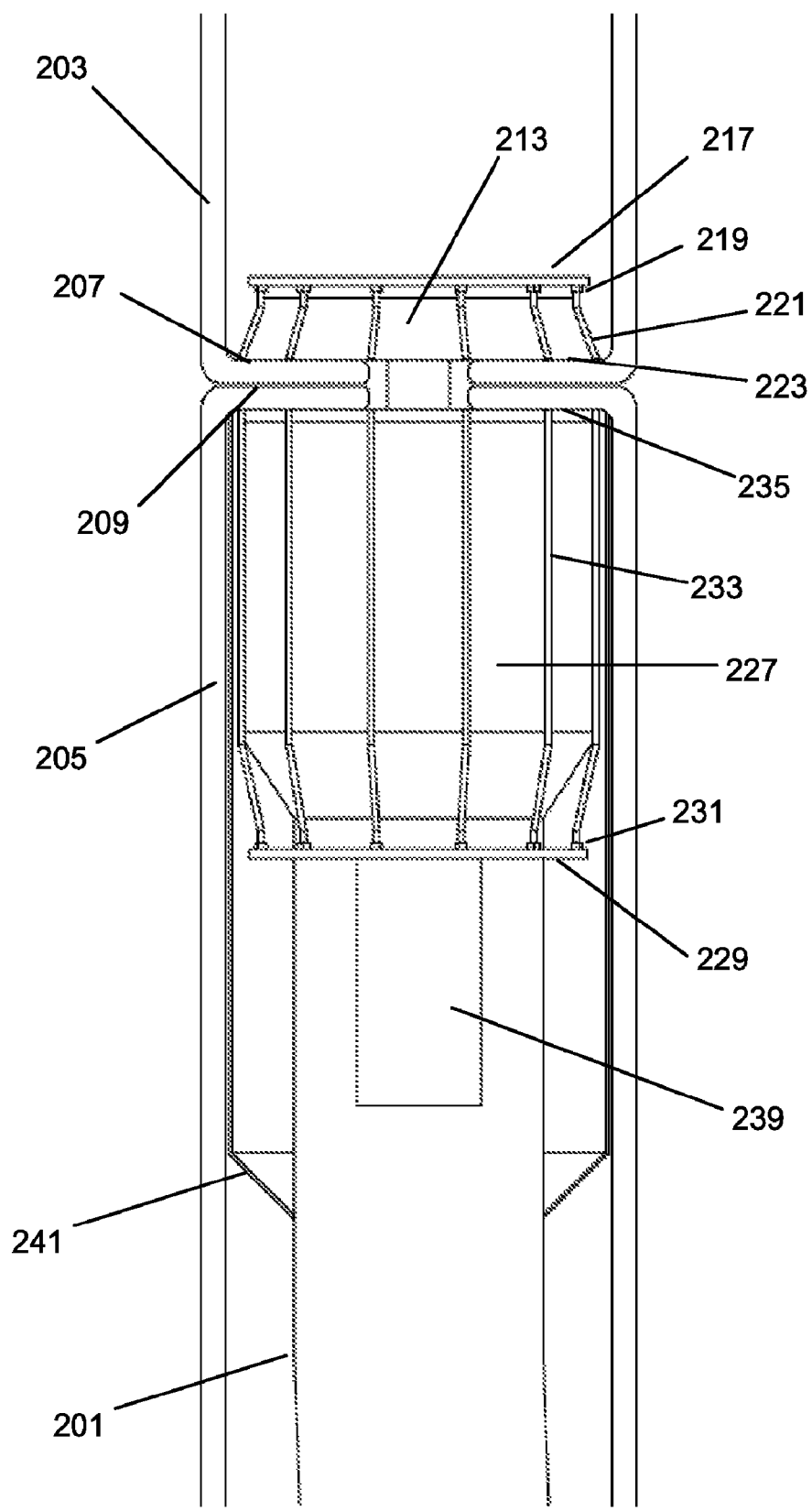
FIG. 2 shows a dual-sided sensing stapler configuration

FIG. 2 depicts a specific configuration of a stapler augmented with sensing capabilities where sensing adjuncts are on both sides of the surgical staple joint. Surgical stapler 201 joins bowel or other segments 203 and 205. The anastomosis is formed by joining tissue flaps 207 and 209. The stapler's anvil 213 lies on the distal end of the anastomosis. Control board and power source 217 lie on anvil 213. Sensor banks 219 are on the face of control board 217. Optical emitters and receivers 219 are coupled optically through light guides or optical fibers 221 to the working surface of the instrument 223 to monitor tissue 207. The described components of the anvil sensing adjunct are enclosed in shell that is optionally coupled to anvil 213.

The stapler's housing 227 lies on the proximal end of the anastomosis. Control board and power source 229 lie on housing 227. Sensor banks 231 are on the face of control board 229. Optical emitters and receivers 231 are coupled optically through light guides or optical fibers 233 to the working surface of the instrument 235 to monitor tissue 209. Additional control board or power source 239 lies on stapler shaft 201 to provide for additional functionality. The described components of housing sensing adjunct are enclosed in shell 241.

Figure 3:
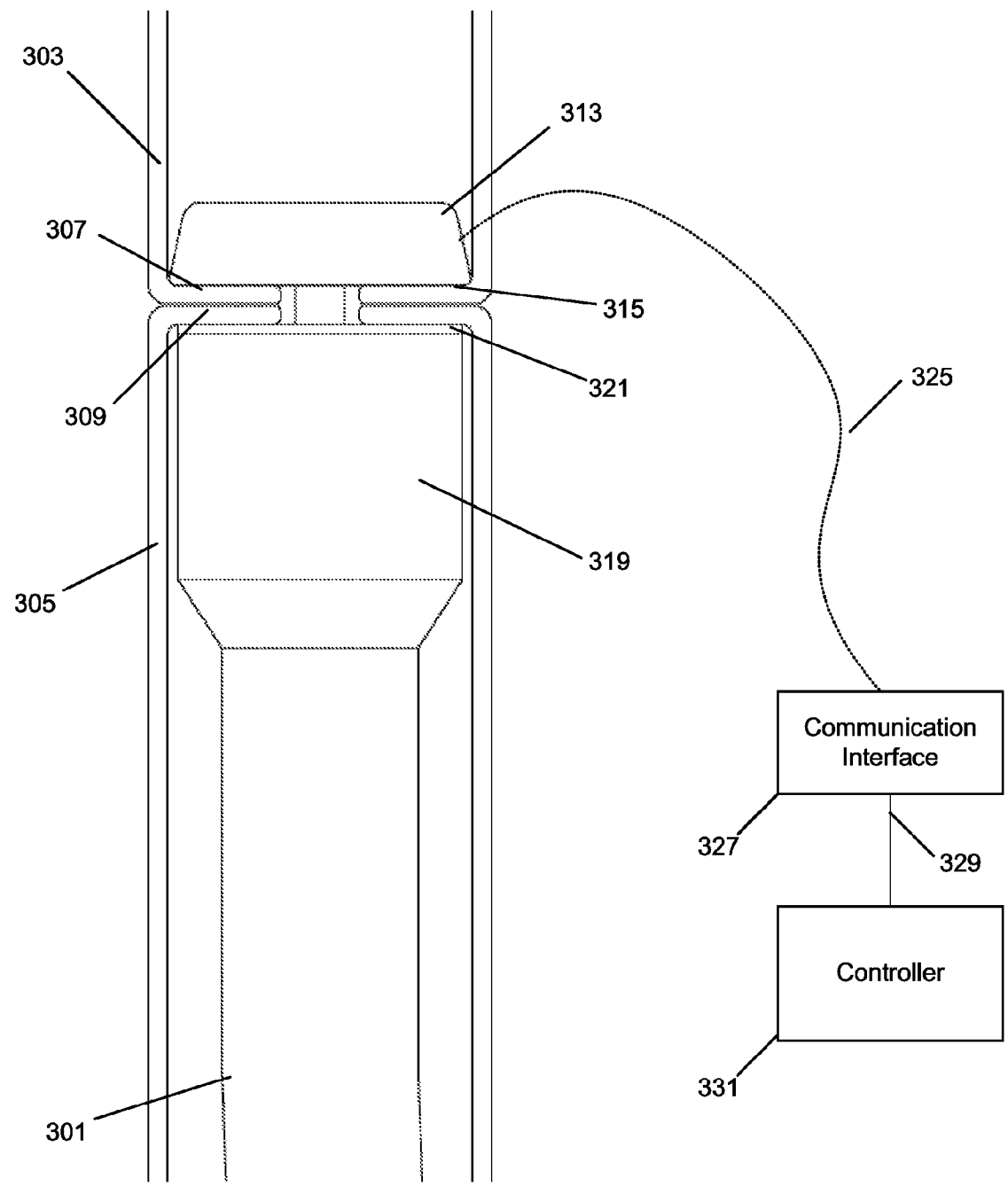
FIG. 3 shows an anvil-only configuration of a sensing stapler

FIG. 3 depicts a configuration of a surgical stapler augmented with sensing capabilities located only on the anvil side. The sensor device may take the form of an optionally coupled adjunct to, or serve as a complete replacement of a standard non-sensing anvil of a surgical stapler. Circular surgical stapler 301 joins bowel or other tissue segments 303 and 305. The anastomosis is formed by joining tissue flaps 307 and 309. The stapler's anvil 313 lies on the distal end of the anastomosis. The anvil sensor device incorporates sensing elements to monitor tissues 307 and 309 between the tissue contacting surfaces 315 and 321. Sensing depth may be modulated to distinguish tissue properties of either side 307, or side 309, or both 307 and 309. Stapler housing 319 and the remainder of stapler 301 need no modification from a standard EEA surgical stapling product. Anvil sensing adjunct 313 is communicatively coupled via 325 to communication interface 327 that is in turn communicatively coupled via 329 to controller 331.

Figure 4A:
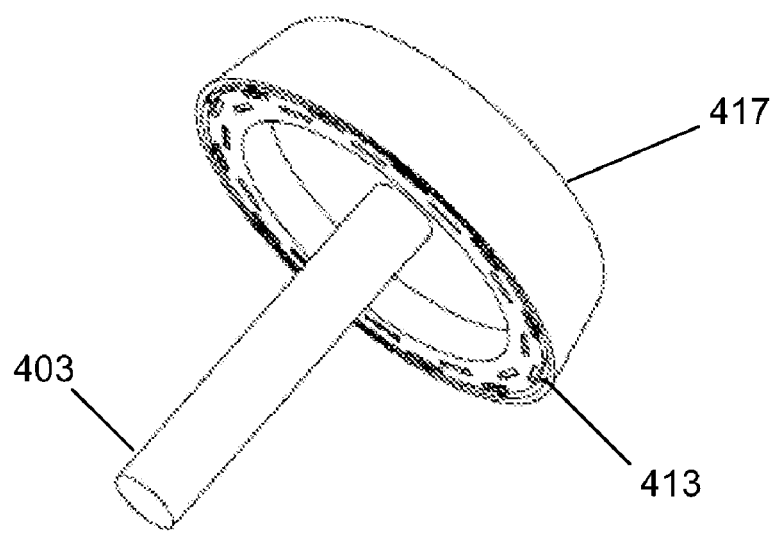
FIG. 4 shows one embodiment of a sensing anvil accessory with light guides
Figure 4B:
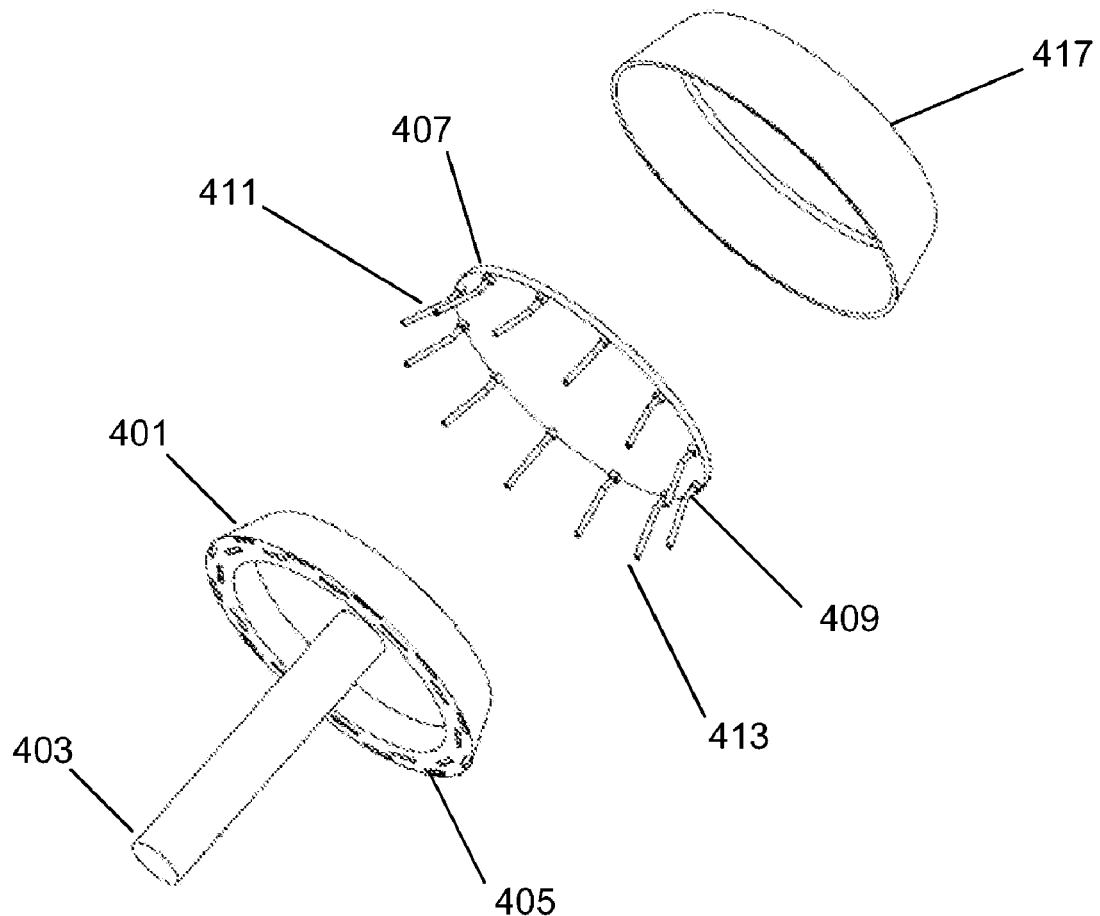

FIG. 4 depicts one embodiment of an anvil sensing adjunct that may present as either an optionally coupled adjunct to, or serve as a complete replacement of a standard non-sensing anvil of a surgical stapler. Anvil 401 couples to the stapler via shaft 403. Staple forms 405 are embedded within the working surface of anvil 401. Control board 407 incorporates sensors 409. Optical sensors and emitters 409 are optically coupled to the working surface via light guides or optical fibers 411. Tips 413 may be shaped to provide appropriate light distribution or specially coated to provide extended sensing capabilities such as determining oxygen quantities by measuring oxygen quenching of fluorescent radiation. The device is sealed inside cap 417.

Figure 5A:
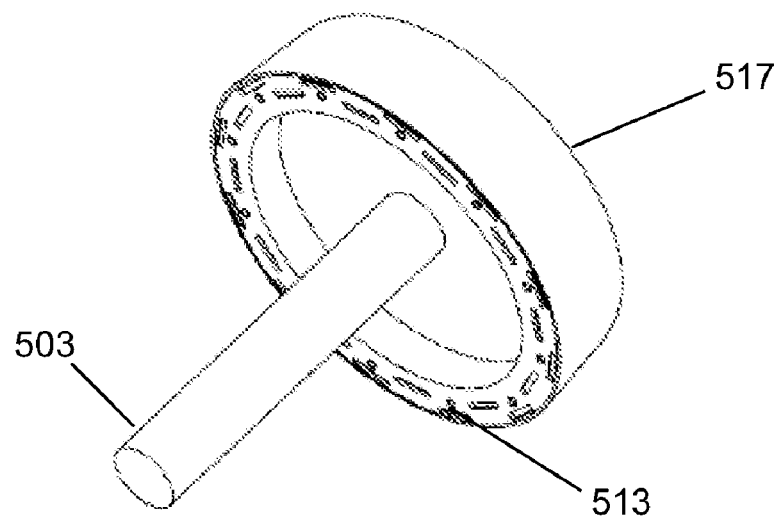
FIG. 5 shows one embodiment of a sensing anvil with light guides
Figure 5B:
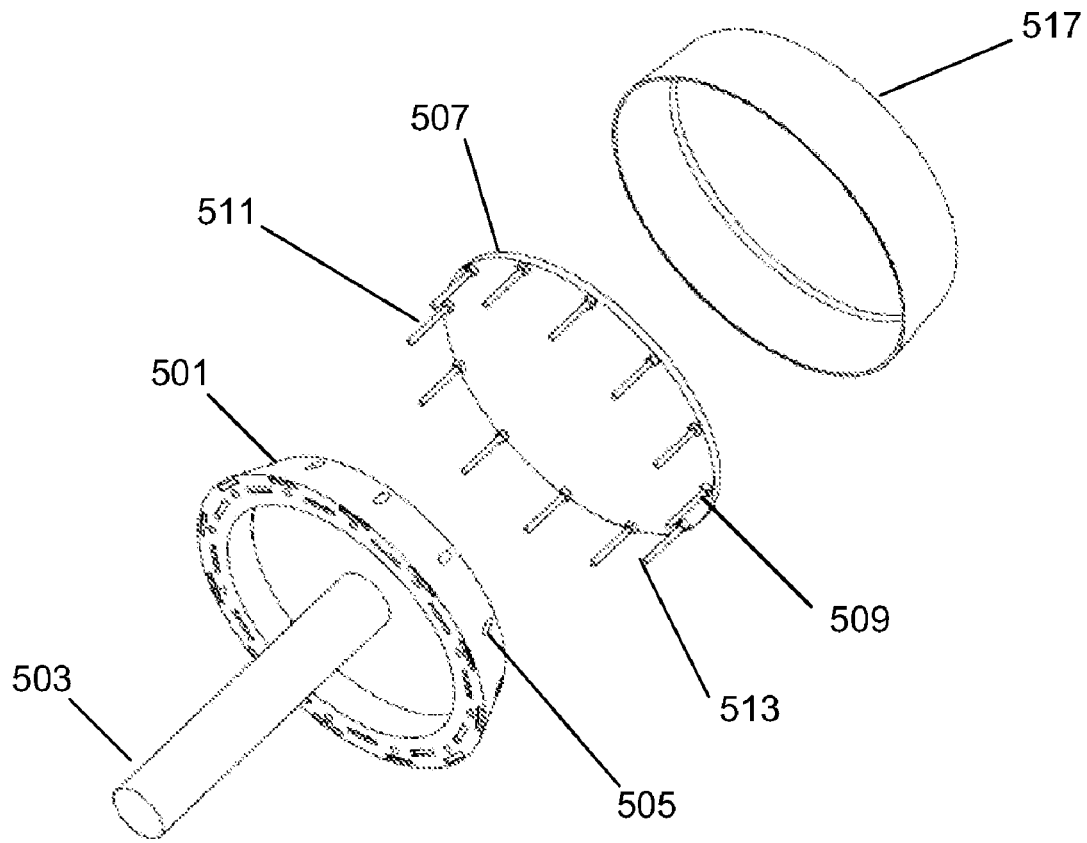

FIG. 5 depicts a further embodiment of an anvil sensing adjunct. Anvil 501 couples to the stapler via shaft 503. Guide-ways 505 provide a path from control board 507 to the working surface of anvil 501 between staple forms 506. Control board 507 incorporates sensors 509. Optical sensors and emitters 509 are optically coupled to the working surface via light guides or optical fibers 513. Tips 513 may be shaped to provide appropriate light distribution or specially coated to provide extended sensing capabilities. Pressure sensors 509 are mechanically coupled by shafts 511 to the working surface to resolve compression forces. The device is sealed inside cap 517.

Figure 6A:
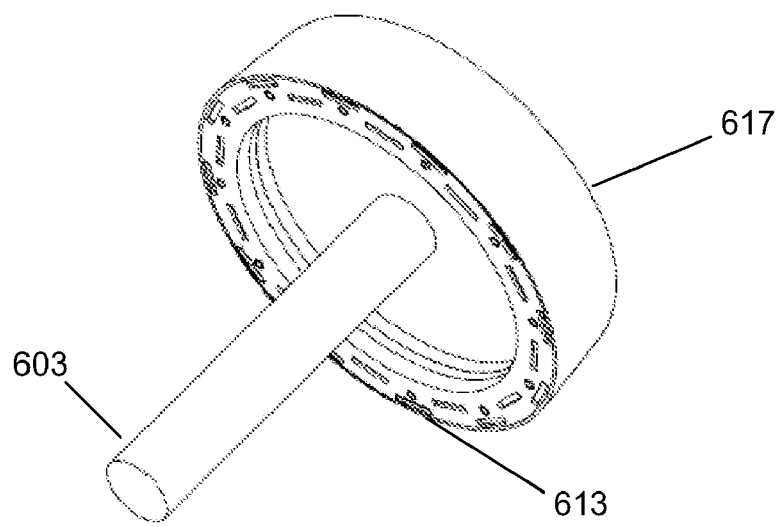
FIG. 6 shows one embodiment of a sensing anvil with integrated pressure sensing
Figure 6B:
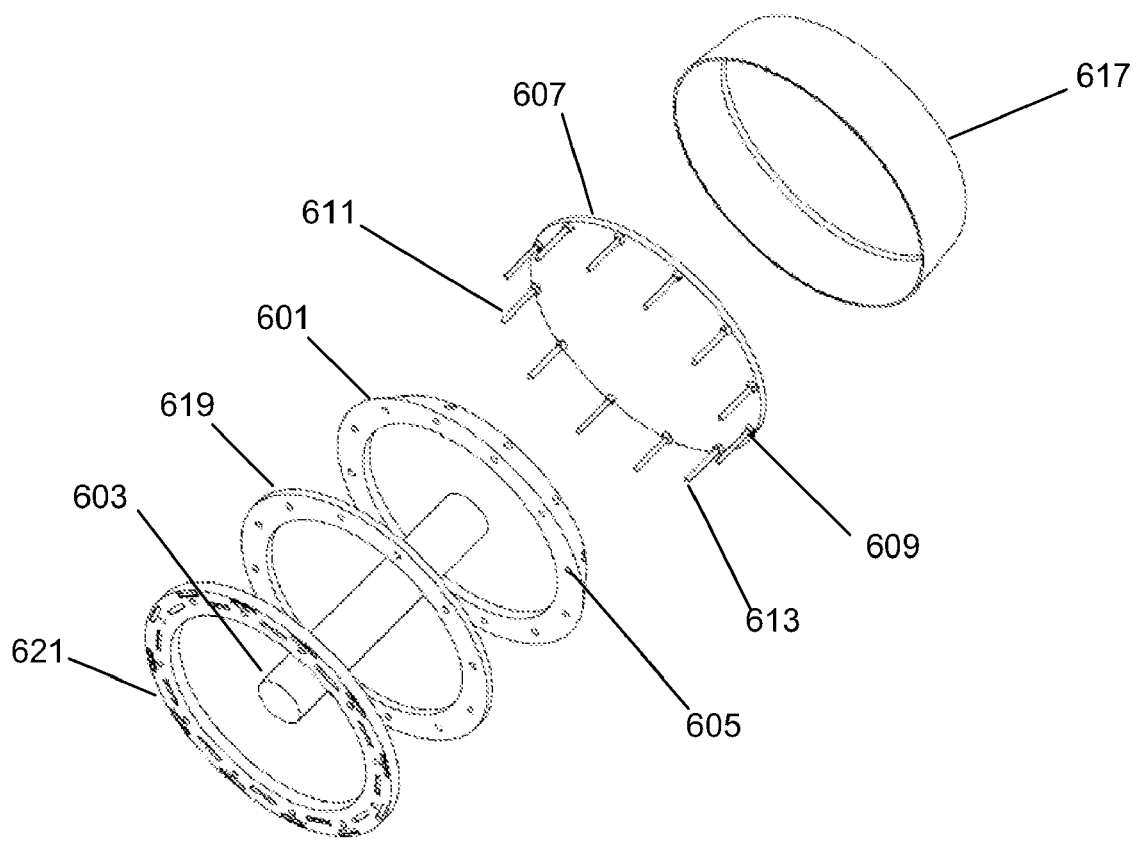

FIG. 6 depicts a further embodiment of an anvil sensing adjunct. Anvil base 601 couples to the stapler via shaft 603. Guide-ways 605 provide a path from control board 607 to the working surface of anvil staple form plate 621. Control board 607 incorporates sensors 609. Optical sensors and emitters 609 are optically coupled to the working surface via light guides or optical fibers 613. Tips 613 may be shaped to provide appropriate light distribution or specially coated to provide extended sensing capabilities. Pressure sensor element 619 measures compression force between anvil base 601 and staple form plate 621 and is communicatively coupled to control board 607. The device is sealed inside cap 617.

Figure 7A:
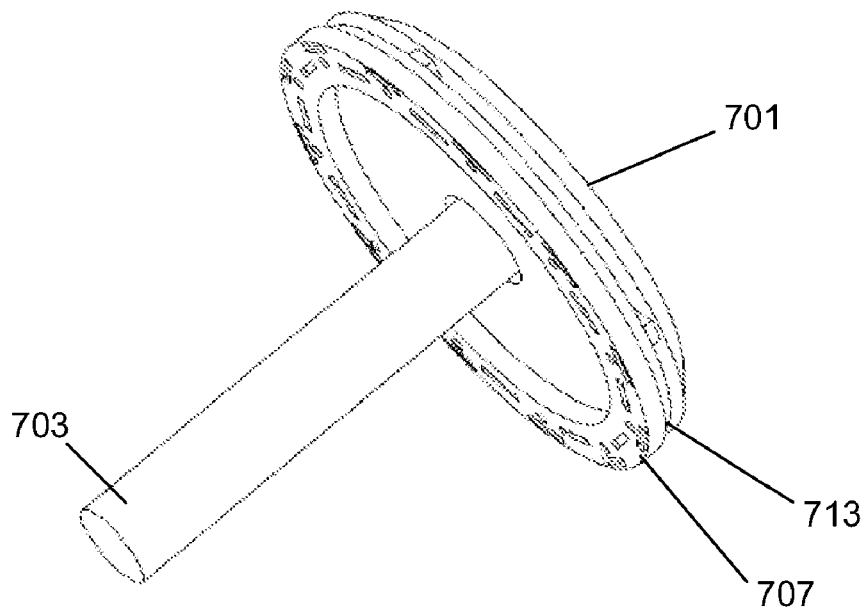
FIG. 7 shows one embodiment of a sensing anvil with pressure sensing at discrete points
Figure 7B:
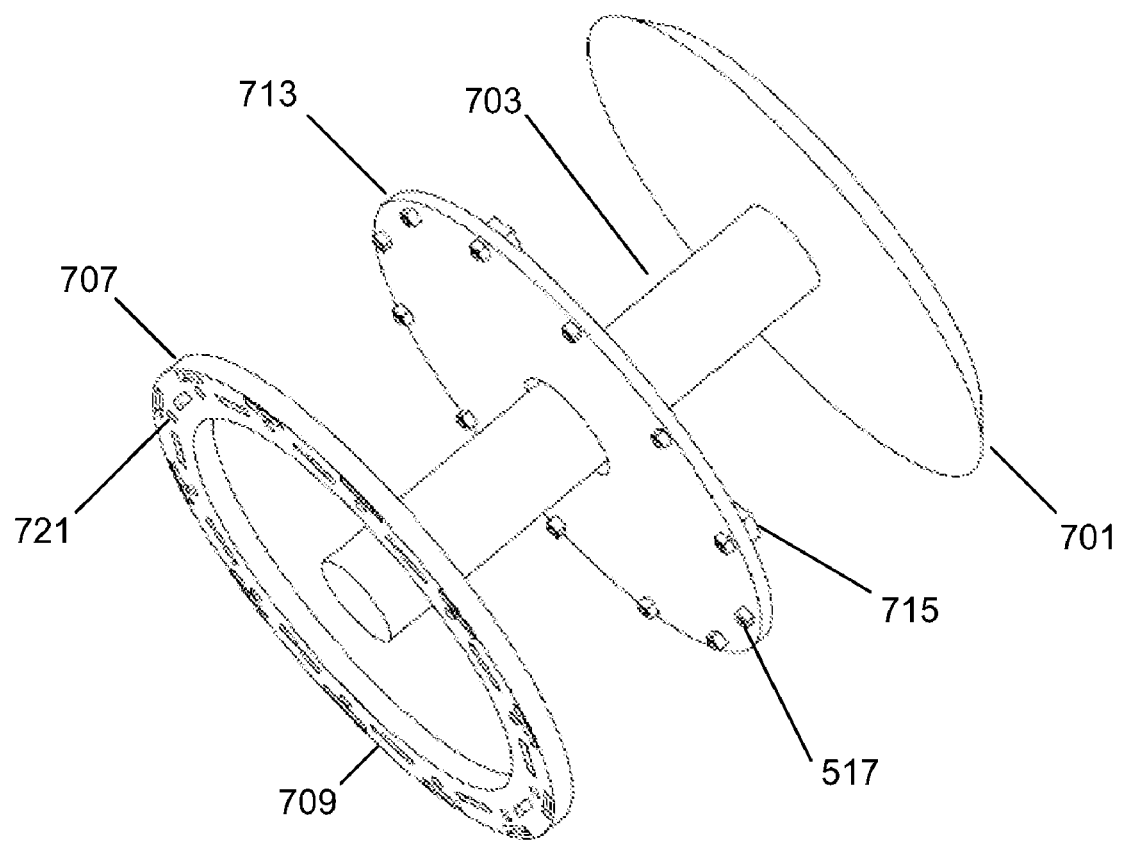

FIG. 7 depicts a further embodiment of an anvil sensing adjunct. Anvil base 701 couples to the stapler via shaft 703. Anvil staple form plate 707 is compressed against the tissue at the working surface 709 by anvil base 701 through control board 713. Attached to control board 713 are pressure sensors 715 on the distal surface and optical sensors 717 on the proximal surface. Optical sensors and emitters 717 lie on staple form plate 707 and are aligned with openings 721. Optical emitters and sensors transmit light and receive light respectively through these openings. The openings can be filled with an optical potting compound or light guides. Control board 713 provides a single electronics board that contains elements for both optical tissue property sensing and compression force sensing. A power source may be incorporated in control board 713 or attached on the distal end of anvil base 701. The power source may be a battery or other source of power. The power source may be single use or rechargeable. Charging may be through a direct electrical connection or an inductive coupling. The components of the anvil sensing adjunct are sealed inside a cap, or alternatively sealed by over-molding or other encapsulation.

Figure 8A:
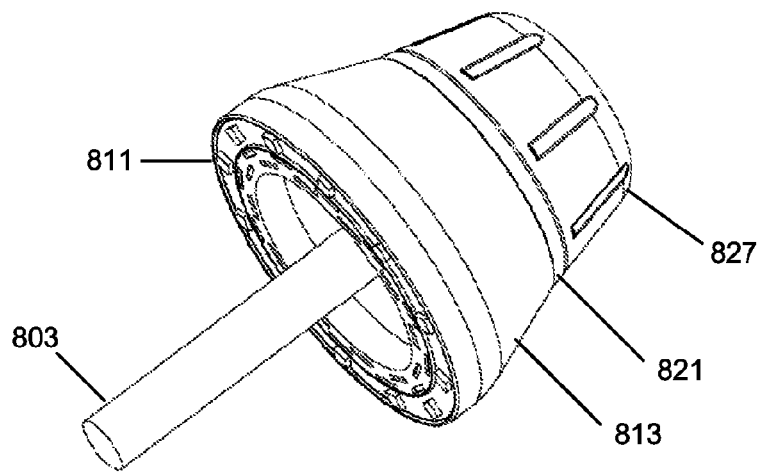
FIG. 8 shows one embodiment of a sensing anvil accessory with sensors at the surface
Figure 8B:
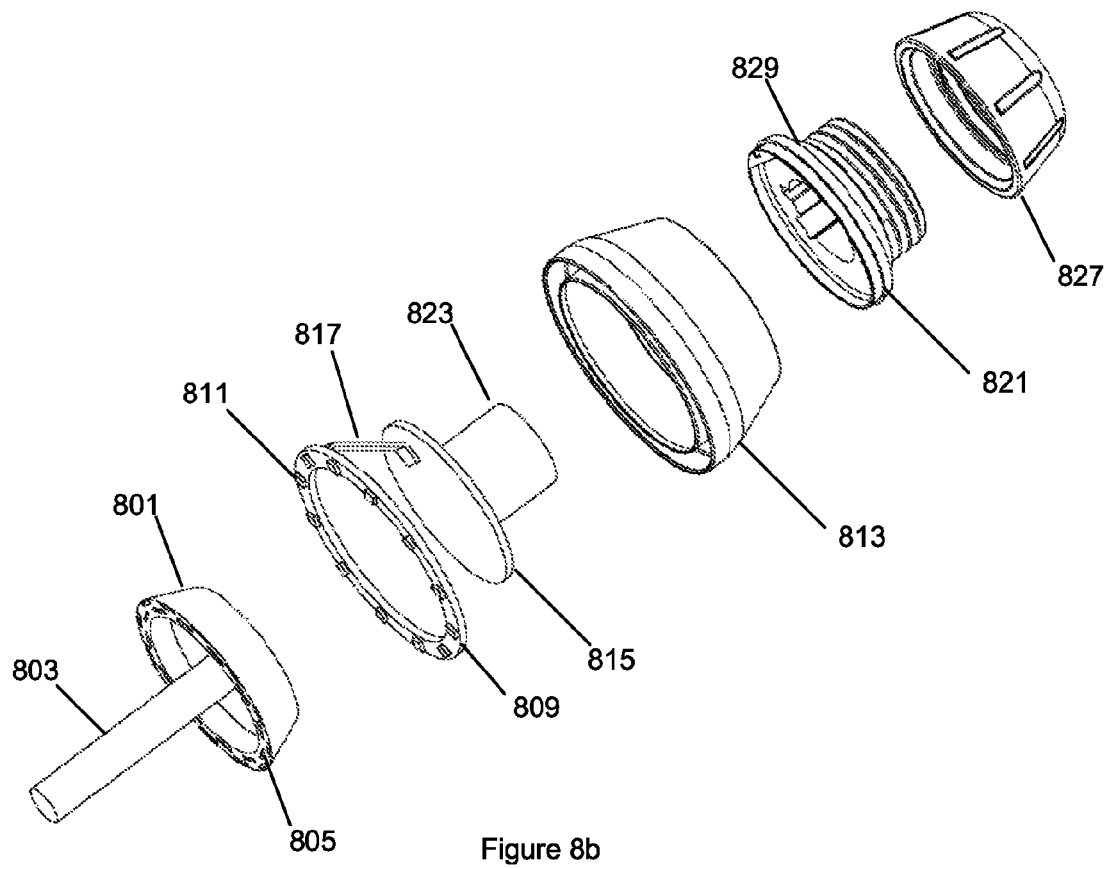

FIG. 8 depicts a further embodiment of an anvil sensing adjunct. The sensing adjunct is an accessory to a standard anvil 801. Anvil 801 couples to the stapler via shaft 803. The working surface (tissue contacting surface) with staple forms 805 contacts tissue at the distal surface of the anastomosis. Sensor ring 809 contains sensor elements 811. Sensor ring 811 fits within lower shell 813 and maintains the sensors 811 flush with working surface 805. In one embodiment, sensor ring contains twelve sets of sensors each including LEDs, photodiodes, and pressure sensors. Surface of sensor ring 811 is sealed with a thin layer of optical encapsulate. In another embodiment the photodiodes or light guides optically coupled to the photodiodes may extend directly to the working surface 805. In this embodiment the surface of the photodiode or light guide may be shaped to provide appropriate light distribution or specially coated to provide extended sensing capabilities such as determining oxygen quantities by measuring oxygen quenching of fluorescent radiation. Flexible cable 817 couples sensor ring 809 to control board 815 mounted within lower housing 813. Control board 815 contains a processor, wireless communications interface, memory, power regulator, led driver, analog sensor input and indicators. Upper shell 821 covers and seals control board 815 and provides a screw thread for cap 827. Battery 823 powers the sensor and is replaceable by removing cap 827. Cap 827 seals the sensor with o-ring 829.

Figure 9:
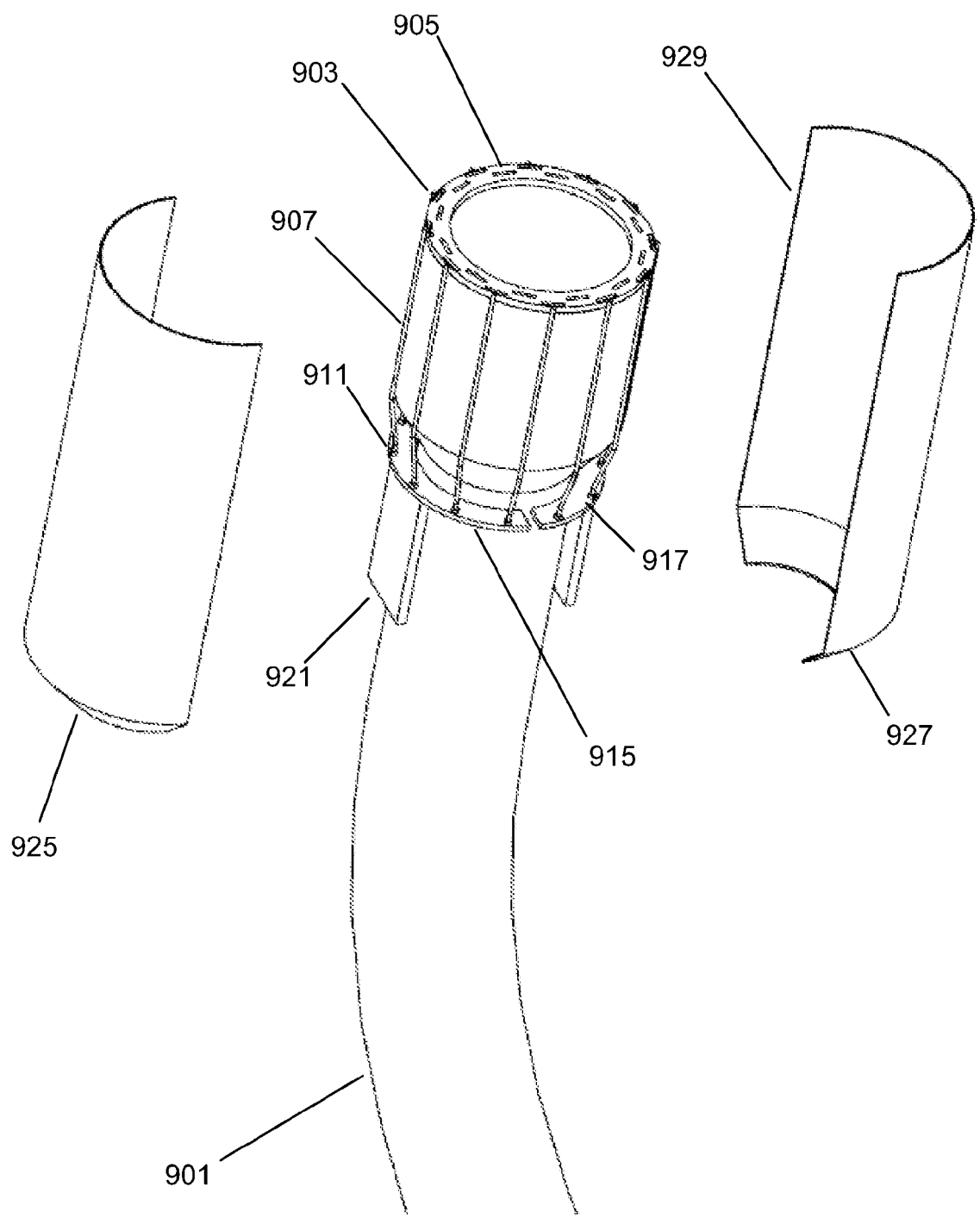
FIG. 9 shows one embodiment of a sensing housing accessory with light guides

FIG. 9 depicts an embodiment of a housing sensing adjunct. Stapler 901 contacts the tissue at the proximal side of the anastomotic junction at surface 905. In one embodiment, the adjunct is split into halves. The sensor boards 915 and 917 contain sensor elements 911. These sensor elements may contain optical sensors incorporating LEDs and photodiodes. Control boards 921 extend from 915 and 917 to provide additional space for electronics, communications, and power sources. Optical sensor elements (including optical emitters and receivers) 911 are coupled to the working surface 903 by light guides or optical fibers 907. The tips 903 may be shaped to provide appropriate light distribution or specially coated to provide extended sensing capabilities such as determining oxygen quantities by measuring oxygen quenching of fluorescent radiation. Shell halves 925 and 927 enclose the described sensor components. The two halves are sealed independently and joined at hinge joint 929. The two halves close around stapler 901.

Figure 10A:
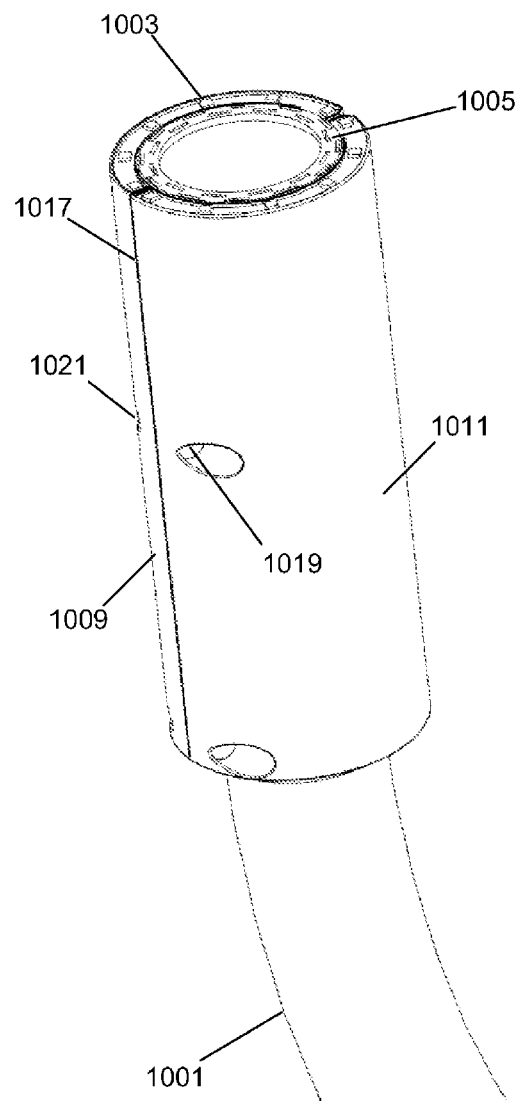
FIG. 10 shows one embodiment of a sensing housing accessory with sensors at the surface
Figure 10B:
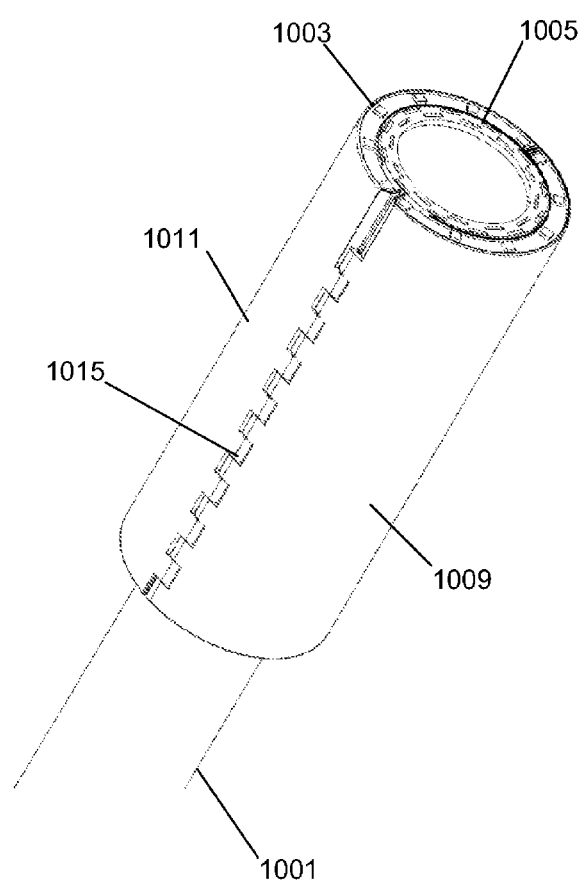
Figure 10C:
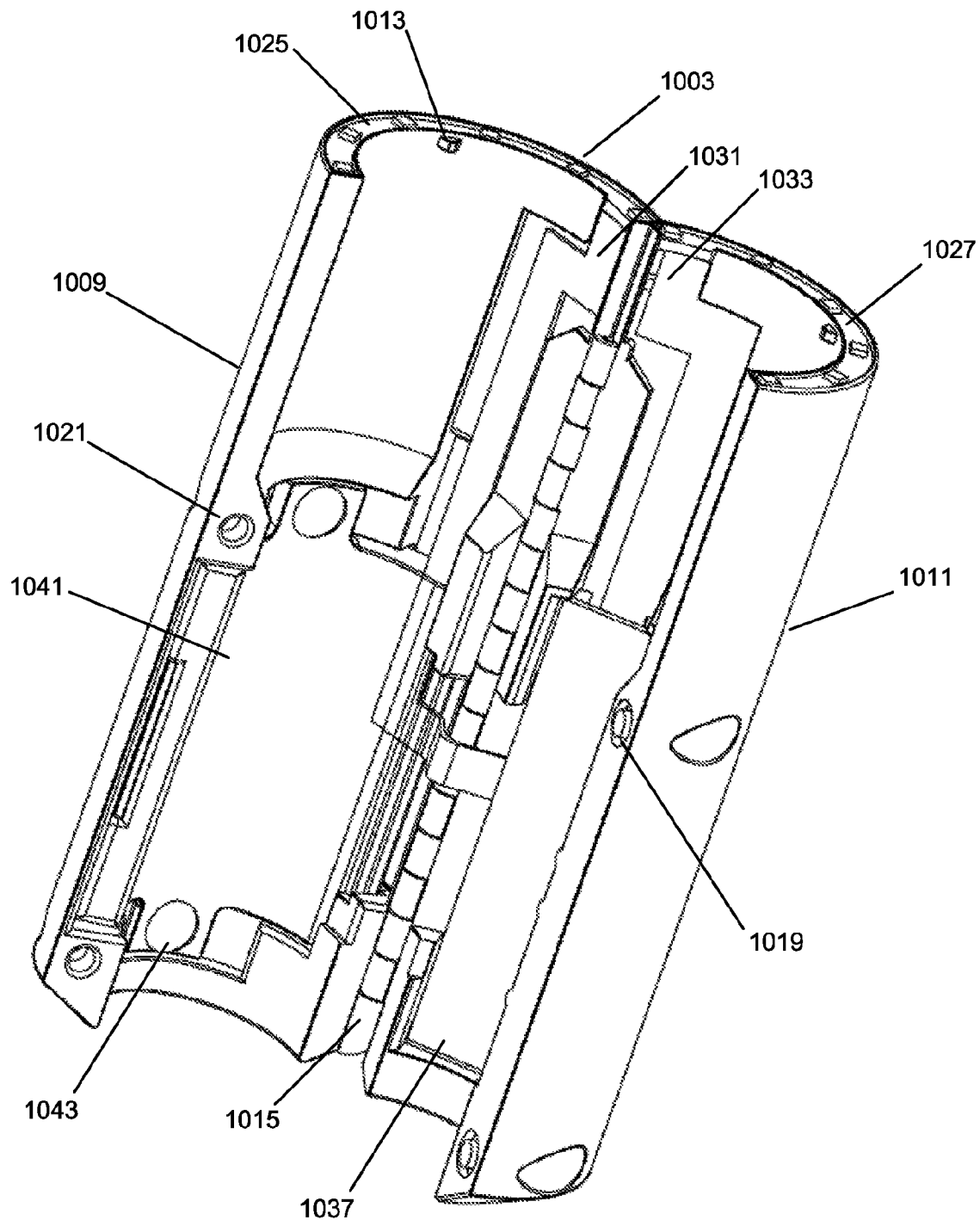

FIG. 10 depicts a further embodiment of a housing sensing adjunct. Stapler 1001 contacts the tissue at the proximal side of the anastomotic junction at surface 1003. Sensor banks 1005 lie flush with the working surface of the stapler 1003. The sensor is split into two halves 1009 and 1011. The two shells 1009 and 1011 are connected at hinge joint 1015 and close around stapler 1001. Tabs 1013 ensure alignment of the sensor to the stapler. The housing sensing adjunct is optionally coupled to the stapler 1001 with screws 1019 and nuts 1021 or a clip or other fastening device. Sensor boards 1025 and 1027 lie inside the top cavity of shells 1009 and 1011. Sensor elements 1005 lie on top of sensor boards 1025 and 1027. In one embodiment, sensor boards 1025 and 1027 contain six sets of sensor banks, each incorporating LEDs, photodiodes, and pressure sensors. In one embodiment the surface of sensor boards 1025 and 1027 is sealed with a thin layer of optical encapsulate. In another embodiment the photodiodes or light guides optically coupled to the photodiodes may extend directly to the working surface 1003. In this embodiment the surface of the photodiode or light guide may be shaped to provide appropriate light distribution or specially coated to provide extended sensing capabilities such as determining oxygen quantities by measuring oxygen quenching of fluorescent radiation. Flexible cables 1031 and 1033 connect sensor boards 1025 and 1027 to control board 1037. Control board 1037 may be a flexible circuit board fit within shells 1009 and 1011. Battery 1041 fits within shell 1009 and locks in place with screws or latches 1043. Battery 1041 seals against the flex cables preventing and leaks when locked in place. All other components are fully sealed.

Figure 11:
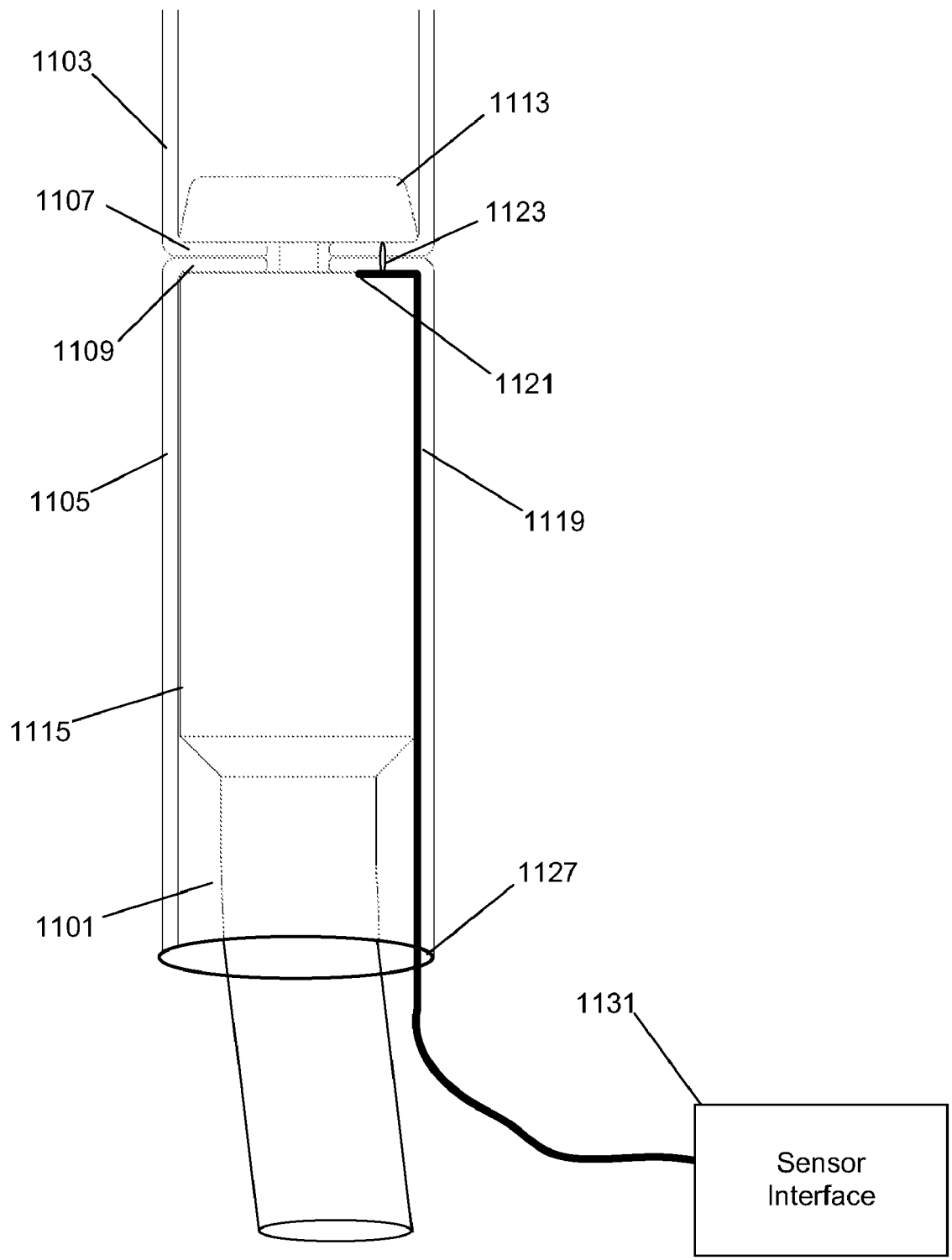
FIG. 11 shows one embodiment of a postoperative monitor

FIG. 11 depicts a sensor for intra-operative and post-operative monitoring of tissue, specifically tissue at an anastomotic junction. In one embodiment, stapler 1101 joins bowel segments 1103 and 1105. Tissue flaps 1107 and 1109 are joined at the staple joint between stapler anvil 1113 and stapler housing 1115. Stapler anvil 1113 and stapler housing 1115 may be traditional components, or part of a sensing surgical stapler. Connection 1119 couples sensor tip 1121 to sensor interface 1131. Connection 1119 may be an electrical connection to compact sensor 1121, or it may be a fiber optic connection to sensor tip 1121. In one embodiment, sensor 1121 is mounted on a bioabsorbable patch that is stapled into place during the anastomosis by staples 1123. In another embodiment, sensor 1121 is fastened by a bioabsorbable clip 1123. In the case of an anastomotic junction of the large bowel, connection 1119 passes out the anus 1127 to sensor interface 1131. Connection 1119 may be bioabsorbable such that it breaks away after a period of time. Alternatively, connection 1119 may be able to be pulled to cause the sensing tip to detach from the sensing site.

Figures 12A, 12B:
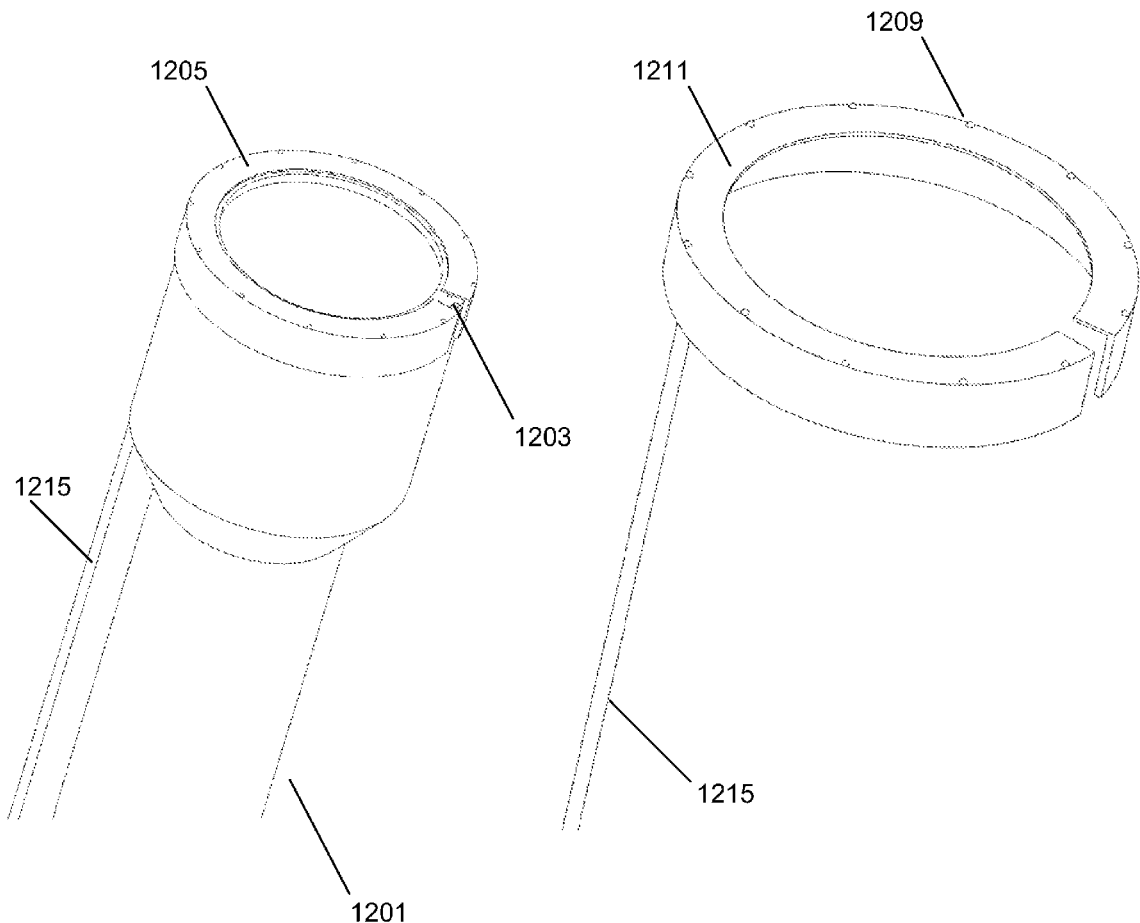
FIG. 12 shows another embodiment of a postoperative monitor

FIG. 12 depicts an alternate embodiment for and intra-operative and post-operative tissue monitor. Stapler housing 1201 performs staple joint at surface 1203. Sensor clip 1205 sits on stapler surface 1203. Sensing elements 1209 monitor tissue properties circumferentially around the staple joint. Flap 1211 lies over stapling surface 1203 and is fastened in place as the anastomosis is formed. The material of 1211 may be bioabsorbable. Optical fibers or other connection 1215 couple the sensing elements 1209 to a sensor interface. The gap in 1205 allows radial expansion of the anastomotic joint to allow for expansion of the bowel lumen so that the anvil and fecal matter may pass. Similarly, one or more sensors can be placed circumferentially on the tissue contacting surface of an endoluminal compression anastomosis ring.

Figure 13:
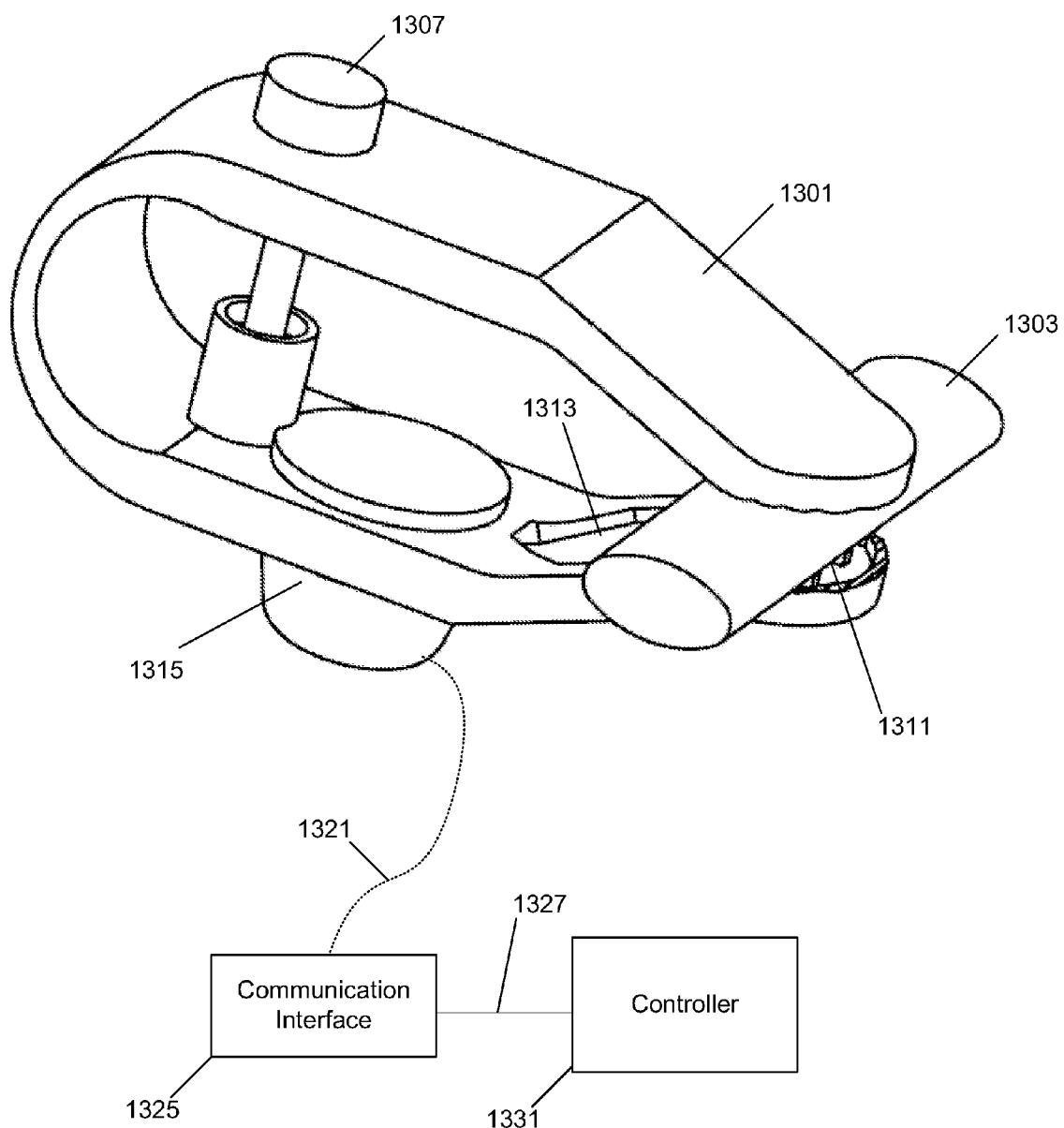
FIG. 13 shows one embodiment of a reference sensor

FIG. 13 depicts one embodiment of a reference sensor device. The reference sensor device 1301 clamps on tissue 1303. In one embodiment, tissue 1303 is healthy bowel tissue used as a baseline measurement from which to compare sensor readings at the surgical site. In another embodiment, reference sensor is used to interrogate tissue and determine tissue viability for planning or monitoring of a procedure. Knob 1307 adjusts the clamping pressure on tissue 1303. Sensors 1311 interrogate the tissue. These sensors may be the same as those on the corresponding sensing surgical instrument or of another type. In one embodiment, two sets of sensors 1311 include photodiodes, LEDs, and pressure sensors for the purpose of measuring tissue oxygen saturation, blood perfusion, and compression pressure on the tissue. Flexible circuit board 1313 supports the sensors 1311 and couples them to the control board within cavity 1315. Cap 1317 seals in the control board and power source. In one embodiment, reference sensor 1301 is communicatively coupled via a wireless link 1321 to communication interface 1325, which is in turn coupled via 1327 to controller 1331. Controller 1331 may receive signals from one or more reference sensors and other sensor devices to make an assessment of the surgical procedure. Alternatively, reference 1301 may directly communicate wirelessly with other sensor devices in a stand-alone mode. In the stand-alone mode with no external display, indicators on the reference provide feedback to the operative team responsive to the tissue analysis.

Figure 14:
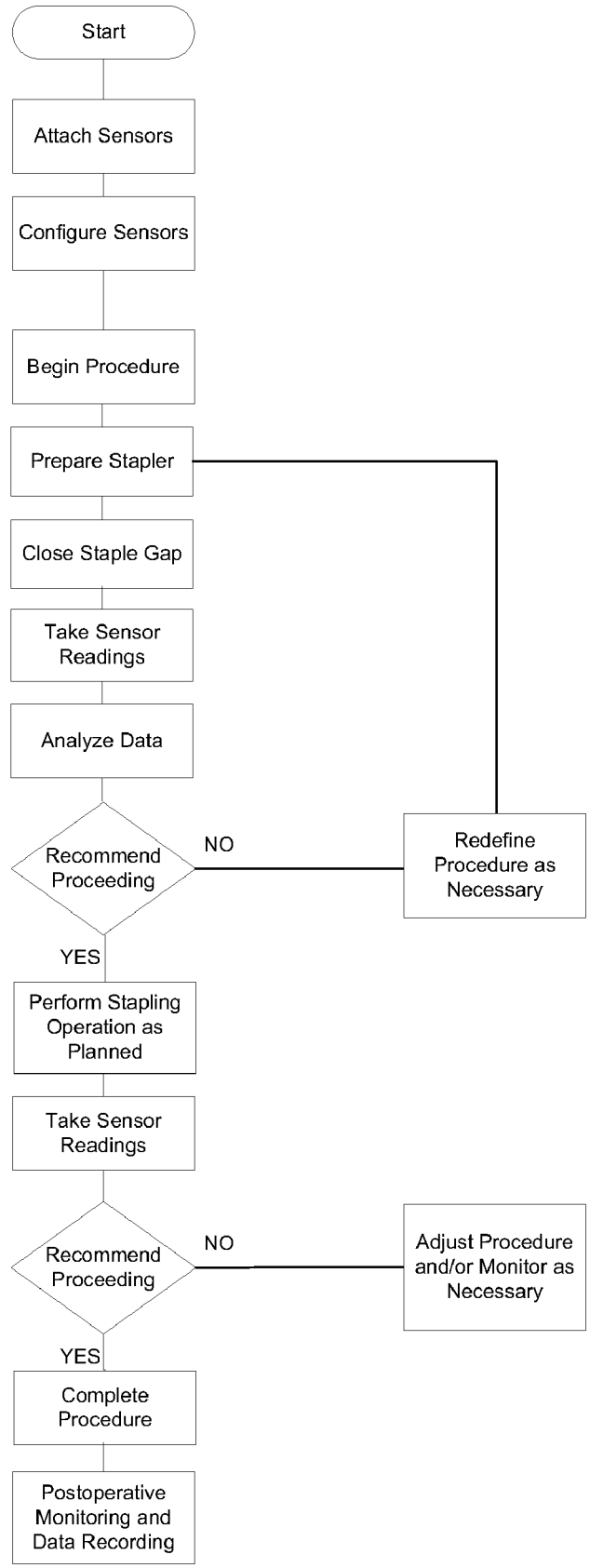
FIG. 14 shows a flowchart for one embodiment of the system use in a procedure

FIG. 14 is a flowchart for one inventive embodiment of the system comprising sensing adjuncts coupled to surgical instruments. Sensing adjuncts are coupled to the surgical instruments and the reference sensor is placed. The sensors are configured appropriately. The stapler is placed at the surgical site and gap is closed. Sensor readings are obtained and analyzed, optionally responsive to a reference sensor or database. The system indicates the likelihood of success of the procedure with the current conditions. The procedure can be adjusted or performed as planned. After performing the procedure, such as a circular anastomosis of bowel tissue, further sensor readings are taken. Sensor readings are analyzed and the system indicates the likelihood of a successful outcome based on the current conditions. The operative team may make adjustments to the operative plan, or complete the procedure. Optionally sensors may be placed at the surgical site for continuous post-operative monitoring.

The optical sensors described in the embodiments may take one several forms. In one form, light emitting diodes or other light sources illuminate tissue and light receivers receive the signal. The light receivers can be photodiodes, photodiode arrays, avalanche photodiodes, photomultiplier tubes, linear and two dimensional CCDs, CMOS sensors, spectrometers, or other sensor types. This may be used for oximetry or spectroscopy type measurements. Wavelengths centered near 660 nm, 800 nm, and 950 nm are used in one embodiment for oximetry measurements; other combinations of two or more wavelengths may also be used. In another embodiment, wavelengths near 680 nm 720 nm, 760 nm, and 800 nm are used to make measurements based on first or second derivative spectroscopy; other discrete wavelengths or a multispectral light source may also be used to generate the differential or second differential spectroscopy signal. Additionally, light sources may be used to illuminate tissue infused with a fluorescent dye to monitor perfusion. This monitoring may be done by either an intensity based measurement or a time-resolved measurement. In a further embodiment, the tips of sensors may be coated with a material such as Ruthenium to determine oxygen quantities by measuring oxygen quenching of fluorescent radiation. The coating may be illuminated to cause it to fluoresce and measurements may be made on intensity-based or time-resolved measurements.

The sensors described in the embodiments above can be used to perform said oximetry-type and/or fluorescence-type sensing. These techniques can be combined with other sensing modalities including optical sensors, electrical sensors, chemical sensors, mechanical sensors, electromechanical sensors, MEMS sensors, nano sensors, biochemical sensors, acoustic sensors, immunologic sensors, fluidic sensors, micro-dialysis based sensors or other types of sensors. The sensors may sense electrical properties, chemical properties, general health, tissue oxygenation, blood oxygenation, pulse rate, pulse presence, pulse rhythm, tissue perfusion, staple gap, compression force, tissue interaction force, staple tension, grasping forces, fluorescence, tissue electrical impedance, tissue electrical activity, pH, concentration of cellular respiration metabolites (e.g. lactic acid), electromyography, temperature, fluid flow rate, fluid flow volume, tissue pressure, blood pressure, biomarkers, radiotracers, immunologic characteristics, biochemical characteristics, nerve activity, an evoked potential, oxygen delivery, oxygen utilization, tissue characterization, tissue general health, tissue flow dynamics, tissue chemical composition, tissue immunologic activity, tissue pathogen concentration, tissue water content, blood hemoglobin content, tissue chromophore content (e.g. hemoglobin), tissue neoplastic cell content and tissue dysplastic cell content, and/or other parameters. The sensing modalities may be implemented using techniques known to those skilled in the art.

The embodiments described above demonstrate how the sensing adjuncts integrate with a circular stapler. These embodiments are for meant as illustrative purposes. The sensing adjuncts can be adapted to provide the described functionalities for other surgical staplers, and other surgical instruments.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention can be practiced without resorting to the details specifically set forth. In other instances, well known processing structures have not been described in detail, in order not to unnecessarily obscure the present invention.

Only an exemplary embodiment of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. A self contained adjunct sensing system configured to be detachably coupled to a surgical stapler, the adjunct sensing system comprising:
    an adjunct housing configured to be detachably coupled to the surgical stapler;
    wherein the adjunct housing maintains
        at least one sensor configured to sense at least one property of tissue and an interaction with tissue;
        a processor configured to receive and process signals from said at least one sensor; and
        a communications interface configured to transfer information at least one of to and from the processor.

2. The adjunct sensing system of claim 1, wherein said at least one sensor comprises at least one of a chemical sensor, a mechanical sensor, an electrical sensor, an optical sensor, and an acoustic sensor; wherein the sensor is configured to measure at least one of a property of tissue and an interaction with a living tissue.

3. The adjunct sensing system of claim 2, wherein the adjunct sensing system takes the form of a surgical stapler anvil that serves to act in place of a non-sensing surgical stapler anvil.

4. The adjunct sensing system of claim 2, wherein the adjunct sensing system takes the form of a member that is detachably coupleable to the anvil or body of a surgical stapler.

5. The adjunct sensing system of claim 2, wherein the adjunct sensing system senses at least one of tissue oxygenation, blood oxygenation, pulse rate, pulse presence, pulse rhythm, tissue perfusion, staple gap, compression force, tissue interaction force, fluorescence, tissue electrical impedance, tissue electrical activity, pH, concentration of cellular respiration metabolites, electromyography, temperature, fluid flow rate, fluid flow volume, tissue pressure, blood pressure, biomarkers, radiotracers, immunologic characteristics, biochemical characteristics, nerve activity, an evoked potential, oxygen delivery, oxygen utilization, tissue characterization, tissue general health, tissue flow dynamics, tissue chemical composition, tissue immunologic activity, tissue pathogen concentration, tissue water content, blood hemoglobin content, tissue chromophore content, tissue neoplastic cell content and tissue dysplastic cell content.

6. The adjunct sensing system of claim 4, where said member comprises one of a sleeve, clip, cap, and shell.

7. The adjunct sensing system of claim 2, wherein said at least one sensor comprises a plurality of sensors; wherein the sensors are positioned on either side of, adjacent to, or interleaved between, the staples or staple forms.

8. The adjunct sensing system of claim 7, wherein said plurality of sensors includes a plurality of optical sensors directed to the tissue contacting surface of the surgical stapler; wherein optical sensor elements of said optical sensors are mechanically coupled to a substrate; wherein the optical sensor elements are optically coupled to the working surface via optical fiber or other light transmission conduit.

9. The adjunct sensing system of claim 8, wherein the tissue contacting surface of the optical sensors are coated with a fluorescent medium; wherein the fluorescent properties of the medium change responsive to a property of said tissue.

10. The adjunct sensing system of claim 2, wherein said at least one sensor is configured to measure at least one of tissue interaction force, tissue compression force, and tension acting on tissue.

11. The adjunct sensing system of claim 10, wherein said at least one sensor comprises force or pressure sensing elements mechanically coupled to a rigid substrate; wherein tissue interaction force at the working surface is mechanically transmitted to the sensor elements.

12. The adjunct sensing system of claim 10, wherein said at least one sensor comprises a pressure sensitive layer comprising at least one of a piezoelectric, resistive, and capacitive film, sheet, or coating.

13. The adjunct sensing system of claim 2, wherein the at least one optical sensor can be modulated to obtain measurements corresponding to multiple tissue depths from the sensor surface by varying at least one of intensity, wavelength, and light emitter to receiver spacing.

14. The adjunct sensing system of claim 13, wherein a sensor placed a single side of an anastomosis is configured to resolve tissue properties for both layers of the apposed tissues.

15. The adjunct sensing system of claim 1, wherein the adjunct sensing system is configured to act independently, or is communicatively coupled via a wireless connection to at least one of an indicator, another sensing device, and a base station.

16. The adjunct sensing system of claim 1, further comprising a power source, wherein the power source is charged without direct electrical contact through an electromagnetic coupling; wherein the adjunct sensing system is hermetically sealed.

17. The adjunct sensing system of claim 1, wherein the adjunct sensing system is configured to quantify staple gap; wherein the adjunct sensing system is a module that optionally mechanically couples to the stapler gap adjustment knob.

18. The adjunct sensing system of claim 1, further comprising a memory configured to store information from at least one of the sensor and the processor.

19. The adjunct sensing system of claim 1, further comprising an indicator.

20. An adjunct configured to be detachably coupled with a surgical stapler, the adjunct comprising:
    an adjunct housing configured to be detachably coupled to the surgical stapler;
    a self contained sensing system, the sensing system including
        at least one sensor;
        a processor configured to receive and process signals from said at least one sensor; and
        a communications interface configured to transfer information at least one of to and from the processor; and
    wherein the self contained sensing system is maintained by the adjunct housing.

21. The adjunct of claim 20, wherein the adjunct housing forms an anvil including a staple form member.

22. The adjunct of claim 21, wherein the staple form member has a substantially circular or semi-circular configuration.

23. The adjunct of claim 21, wherein the staple form member has a substantially linear configuration.

24. The adjunct of claim 20, wherein the adjunct housing is configured to be detachably coupled with an anvil portion of a surgical stapler.

25. The adjunct of claim 20, wherein the adjunct housing is in the form of one of a sleeve, a shell, a cap, or a clip.

26. The adjunct of claim 20, further comprising a memory configured to store information from at least one of the sensor and the processor.

27. The adjunct of claim 20, further comprising an indicator communicatively coupled with said sensing system.

28. The adjunct claim 20, wherein said sensing system is communicatively coupled with at least one reference sensor, which provides a baseline measurement of at least one of a physiologic property of tissue and a mechanical property of tissue.

29. The adjunct of claim 20, further comprising an actuator configured to vary staple gap or height.

30. The adjunct of claim 29, wherein the actuator comprises a motorized actuator.

31. The adjunct of claim 29, wherein the actuator is configured to control an adjustment knob of the surgical stapler.

32. The adjunct of claim 20, further comprising an actuator configured to assist with firing of the surgical stapler.

33. The adjunct of claim 32, wherein the actuator comprises a motorized actuator.

34. The adjunct of claim 20, wherein readings of said at least one sensor are configured to provide information utilized to maintain consistency by one of tissue interaction force, tissue compression force, and tension acting on tissue.

35. The adjunct of claim 20, wherein the sensing system is configured to provide guidance regarding a surgical procedure.

36. The adjunct of claim 35, wherein the guidance predicts success of a surgical procedure.

37. The adjunct of claim 36, wherein the guidance avoids or detects failure of a surgical procedure.

38. The adjunct of claim 20, wherein the adjunct is configured to deliver a therapy to tissue.

39. The adjunct of claim 38, wherein said therapy comprises at least one of photodynamic, pharmaceutical, bioadhesive, brachy-, and nano-therapies.

40. A surgical assembly comprising:
    a device for creating an anastomosis; and
    an adjunct maintained by an adjunct housing, the adjunct housing configured to be removably coupled with the device, the adjunct comprising a self contained sensing system configured to sense at least one of a physiologic property of tissue and a mechanical property of tissue using a sensor, process signals related to said sensed tissue properties using a processor, and transfer information related to at least one of said sensed tissue properties and said processed signals using a communications interface.

41. The surgical assembly of claim 40, wherein said device is a surgical stapler.

42. The surgical assembly of claim 40, wherein said device is a surgical compression anastomosis ring.

\* \* \* \* \*